United States Patent [19]

Shigeura et al.

[11] Patent Number: 5,338,426
[45] Date of Patent: Aug. 16, 1994

[54] HORIZONTAL POLYACRYLAMIDE GEL ELECTROPHORESIS

[75] Inventors: John Shigeura, Fremont; John A. Bridgham, Hillsborough; Louis B. Hoff, Belmont; P. Eric Mayrand, Pacifica, all of Calif.

[73] Assignee: Applied Biosystems, Inc., Foster City, Calif.

[21] Appl. No.: 936,979

[22] Filed: Aug. 28, 1992

[51] Int. Cl.$^5$ ............................................. C25B 9/00
[52] U.S. Cl. ............................................. 204/299 R
[58] Field of Search ........................ 204/299 R, 182.8

[56] References Cited

U.S. PATENT DOCUMENTS 3,719,580  3/1973  Roberts et al. ............... 204/182.8
5,137,613  8/1992  Brumley, Jr. et al. ......... 204/299 R

OTHER PUBLICATIONS

El-Negoumy, "A convenient migration chamber for electrophoresis in solid gels." *J. Chromatog.* 23 (1966) 325–329.

*Primary Examiner*—John Niebling
*Assistant Examiner*—C. Delacroix-Muirheid
*Attorney, Agent, or Firm*—Donald R. Boys; Joseph H. Smith

[57] ABSTRACT

An electrophoresis apparatus has a gel film cast between two plates and buffer reservoirs at each end of the film with electrodes connectable to an external power supply for providing electromotive force for driving electrophoresis. The reservoirs are configured to wet the ends of the gel film and submerge the electrodes with the apparatus positioned either horizontally or vertically, so gel films can be cast horizontally with sample wells formed in the end of the gel between the plates. Samples may be added to the wells and run into the gel with the apparatus positioned vertically, and the analytical separation may be performed with the apparatus again positioned horizontally, such as in an automatic scanning apparatus.

9 Claims, 13 Drawing Sheets

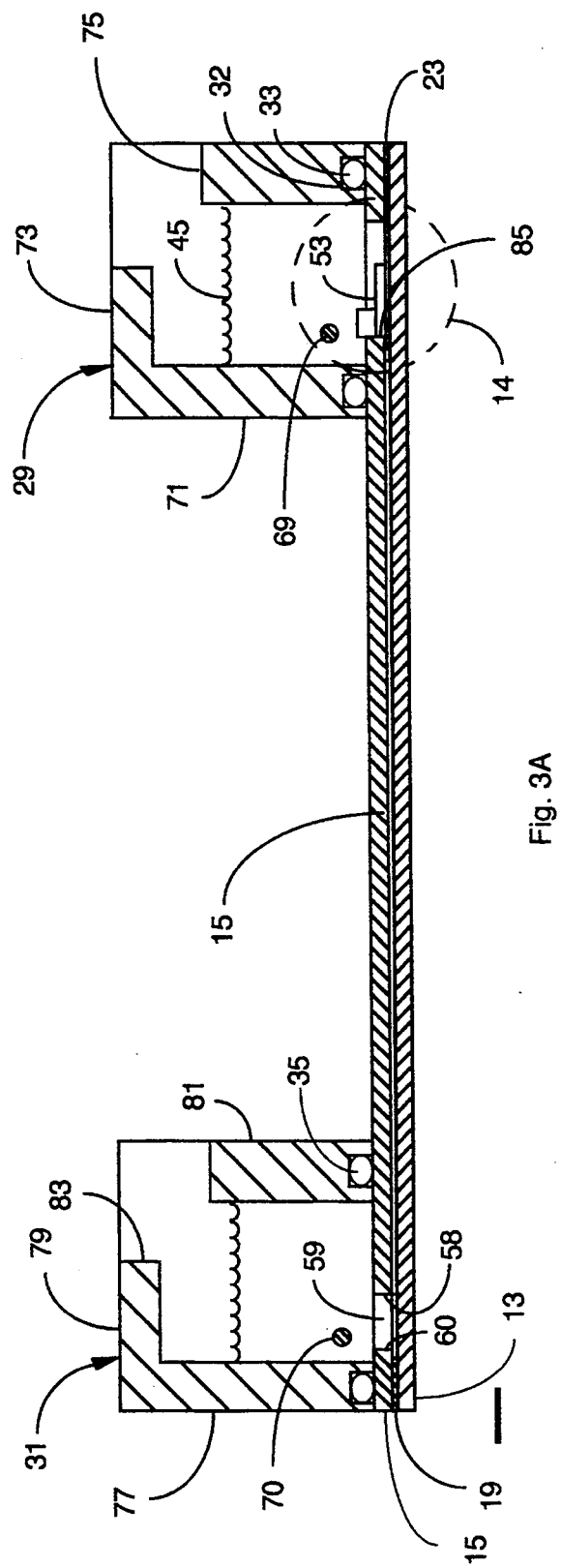
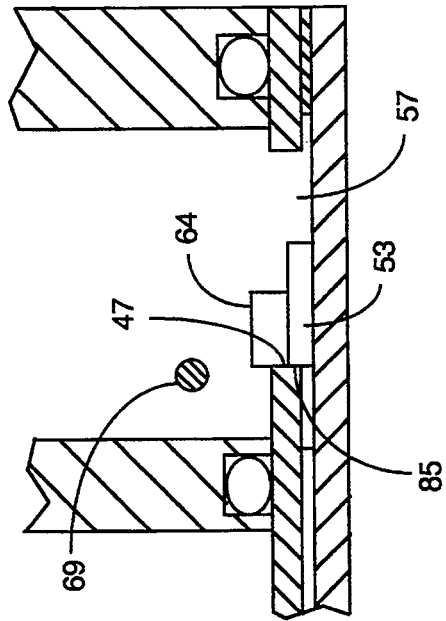
Fig. 3A
Fig. 3B

HORIZONTAL POLYACRYLAMIDE GEL ELECTROPHORESIS

FIELD OF THE INVENTION

This invention is in the field of apparatus and methods for separating macromolecules by electrophoresis, and pertains in particular to polyacrylamide gel film systems.

BACKGROUND OF THE INVENTION

There has been rapid growth in recent years in apparatus and methodology for biochemical enterprise, particularly for cleavage, separation and analysis of macromolecules such as DNA, including human DNA. There are a number of uses, such as determining the presence of genetically induced conditions such as Sickle-Cell Anemia, Huntington's Chorea and others Fluorescent gel scanning has also become important as an identification tool. Genetic code from a human hair or a flake of skin can be matched to a single human being, supplementing older procedures, such as fingerprint analysis in criminal law.

Typically, macromolecules are separated and identified by electrophoresis. It is well known in the art that electrically charged macromolecules of different size and structure move at different velocities in a specific medium under the influence of an electrical field. Typical mediums are agarose slabs and polyacrylamide gel films.

Agarose is a material that can be dissolved in hot water, and the solution formed solidifies to a gel state on cooling, so slabs of agarose can be prepared by pouring warm, liquid material into a structural container and cooling it. Agarose is typically poured in a horizontal slab, open-face. Wells are molded into the upper surface of a slab for introduction of sample, and the slab is immersed in buffer during the electrophoresis operation, Because the slabs are poured in relatively thick sections, such as 5 mm., sample wells of sufficient volume may be formed, Agarose gels are capable of resolving DNA fragments above about 150 base-pairs in size. Much smaller fragments and relatively small macromolecules of other kinds tend to move through agarose more or less unimpeded, so they cannot be resolved with agarose gel systems. For relatively small DNA fragments, below about 500 base-pairs, and for relatively small macromolecules of other kinds, polyacrylamide gels are useful. There is a broad area of overlap in the sizes of macromolecules for which agarose or polyacrylamide is useful.

To prepare a polyacrylamide gel, a solution is prepared with acrylamide, a cross-linking agent, and a buffer, and the catalyst is added just prior to pouring. Polyacrylamide is typically cast in very thin films (0.5 mm is typical), partly because this material requires more electrophoretic driving force than agarose, and is therefore more subject to heating by the passage of current. Because temperature gradients effect macromolecule migration and distort separation patterns, the gels must also be very thin to promote uniform temperature. Moreover, the cross-linked material tends to swell on exposure to buffer solution, so gels are cast between glass plates for structural support and dimensional integrity, to provide minimal exposure to air during polymerization and to buffer solution after polymerization.

Acrylamide polymerization proceeds only in the absence of oxygen, so areas exposed to air do not polymerize to form the gel. Typically buffer contacts only the ends of the very thin polyacrylamide gel film in operation.

Because polyacrylamide gels are usually prepared in thin films, formation of vertical wells in a horizontal film, the well having the depth of the thickness of the film, as is done in agarose systems, is not a suitable arrangement. Such wells are much too small in volume for adequate sample for electrophoresis. For this and other reasons polyacrylamide gels have traditionally been used in vertical systems. Sample wells are cast in the end of the film by inserting a comb before pouring the gel film.

Because agarose gels are typically horizontal systems, scanning apparatus has been developed also in a horizontal format for analyzing separations while electrophoresis is performed. Similarly, since polyacrylamide gels are typically vertical systems, scanning apparatus has been developed for these systems in a vertical format for analyzing separations while electrophoresis is performed. So, to cover all of the range of macromolecule sizes that are typically of interest, it is usually necessary to have gel apparatus of two different kinds, and also scanning apparatus of two different kinds.

Some efforts have been made to provide polyacrylamide electrophoresis apparatus that can be operated in a horizontal mode with scanning apparatus usually used for agarose gels. One way that has been tried involves casting a polyacrylamide gel horizontally between two glass plates, and forming vertical wells at right angles to the gel film at one end. A problem with this arrangement is that the voltage providing the electrophoretic driving force has to be applied from the end of the wells to the end of the film at the opposite end from the sample wells, and the electrical field (and the sample) has to pass around a right angle at the bottom of the well to enter the film. This has been found in practice to be troublesome, and to cause distortions in the separation bands.

To minimize the range and scale of apparatus necessary to cover a suitably broad range of sizes of macromolecules with adequate resolution, what is needed is an apparatus for polyacrylamide gel electrophoresis that can be used with horizontal scanning apparatus, and which does not suffer from the problems of right angle sample injection and the non-uniform patterns that result.

SUMMARY OF THE INVENTION

In an embodiment of the invention an electrophoresis apparatus comprises a first and second plate spaced apart defining a volume for an electrophoretic gel film. A seal means at the periphery of the spaced-apart plates contains a gel forming solution in the volume between the plates, and provides for open ends for the volume, so open ends of a gel cast therein will be exposed. A first and a second reservoir means at the ends are for holding buffer solution for wetting the open ends of a gel cast, and each reservoir has an electrode means positioned to be immersed in buffer solution and connectable to a power supply. The reservoir means are configured so the open ends of a gel and the electrodes are immersed in buffer when the apparatus is positioned with the glass plates horizontal, and also with the apparatus positioned with the glass plates vertical.

In a particular embodiment the plates are substantially flat glass plates, and sealing for containing a gel-forming solution while liquid is accomplished by strips of hydrophobic tape laid along edges between the plates. In this mode, the strips accomplish spacing as well as sealing. In an alternative embodiment, teflon tape is used, and in some embodiments, spacer seals are cut out in the shape of window gaskets, to extend around all the periphery of the spaced-apart plates.

Also in a preferred embodiment, all sides of the spaced-apart plates are sealed, and one plate has openings near the ends extending through the one plate into the region between the plates where a gel is cast. In this embodiment, removable, "clamp-on" reservoirs are provided which align and hold the plates and seal around the openings through the one plate with openings. Buffer in a reservoir thus reaches and immerses the end of a gel film which terminates in each of the openings through the one plate.

In the embodiment with openings through one of the plates, the reservoirs are configured to provide access to the buffer-holding volume with the reservoirs sealed to the plates. This feature allows for poring gel solution, clean-up after gel forms, and for inserting and withdrawing a comb for forming sample wells in the gel between the plates.

In all embodiments the reservoirs are configured to hold buffer, keeping the ends of the gel film and the electrodes immersed, with the apparatus positioned either horizontally or vertically, and having a requirement that a particular one of the reservoirs, with the apparatus positioned vertically, be the lower of the reservoirs.

In an alternative embodiment the glass plates are assembled with seat materials to a plastic molded tray having reservoirs formed in the ends, and also in a manner to immerse electrodes and gel ends whether positioned horizontally or vertically.

In all embodiments, the reservoirs are configured to allow immersion of both gel film ends and electrodes whether the apparatus is positioned vertically or horizontally. This feature allows a gel to be cast horizontally and provided with sample wells in the direction of the film between the glass plates. Once a film is ready, samples may be added and run into the gel with the apparatus positioned vertically, and then the apparatus may be again moved to horizontal for full electrophoresis, and also for analysis of the separation patterns, if needed; such as in an automatic scanning apparatus.

In one embodiment, a unique well-forming comb is provided, having cams for withdrawing the comb from a formed gel at a reduced rate, and with considerably less probability of damaging sensitive strips of gel between sample wells.

BRIEF DESCRIPTION OF THE DRAWINGS

FIG. 3A is a section view taken along line 3A—3A in FIG. 1.

FIG. 3B is an enlargement of the area within dotted circle 14 of FIG. 3A.

DESCRIPTION OF THE PREFERRED EMBODIMENTS

Figure 1:
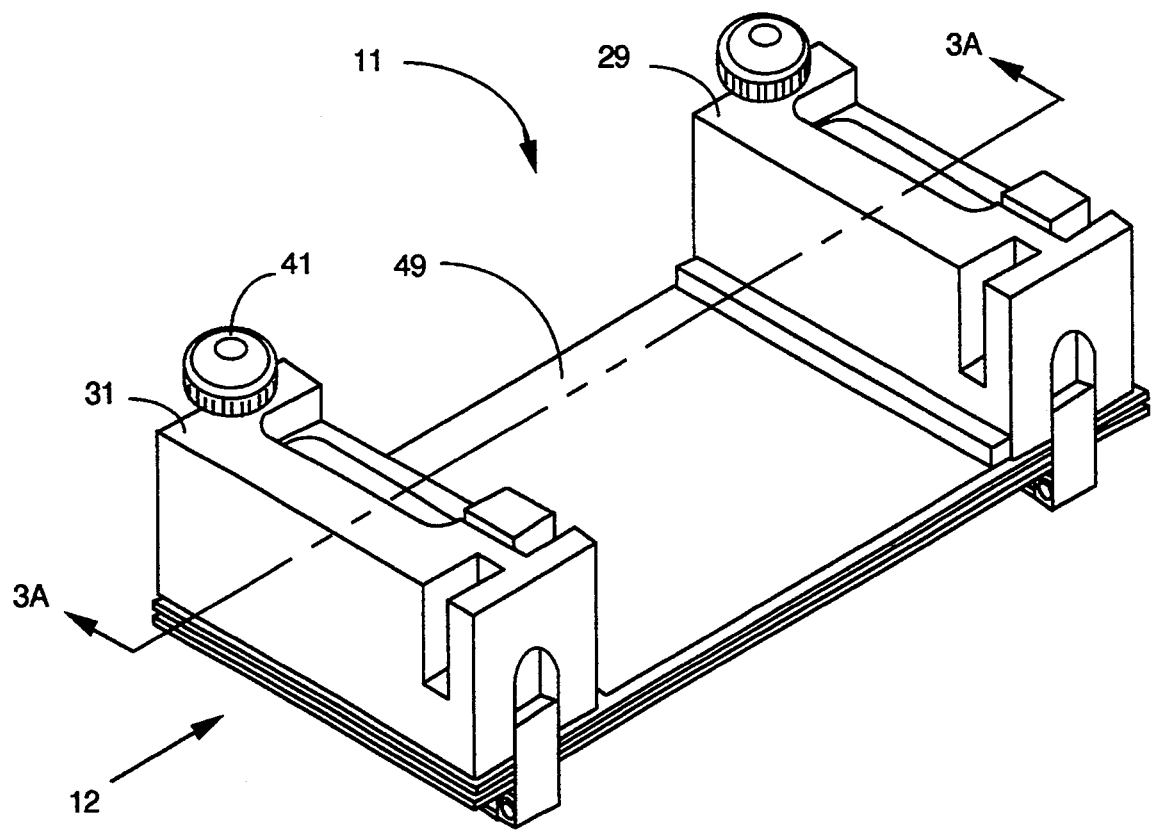
FIG. 1 is an isometric assembly of an embodiment of the invention.

FIG. 1 is an isometric view of an assembled polyacrylamide gel apparatus 11 according to the present invention. In this embodiment a polyacrylamide gel film is cast between glass plates and extends between removable reservoirs that are clamped over the plates at each end. The electrophoresis apparatus in this embodiment is designed to be operable in a horizontal or in a vertical orientation. It can therefore be used in an automated scanner instrument designed for operating either vertically or horizontally. In the present embodiment, the polyacrylamide gel electrophoresis apparatus is designed to be used with the Model 362 Gene Scanner TM manufactured and marketed by Applied Biosystems of Foster City, Calif.

Figure 2:
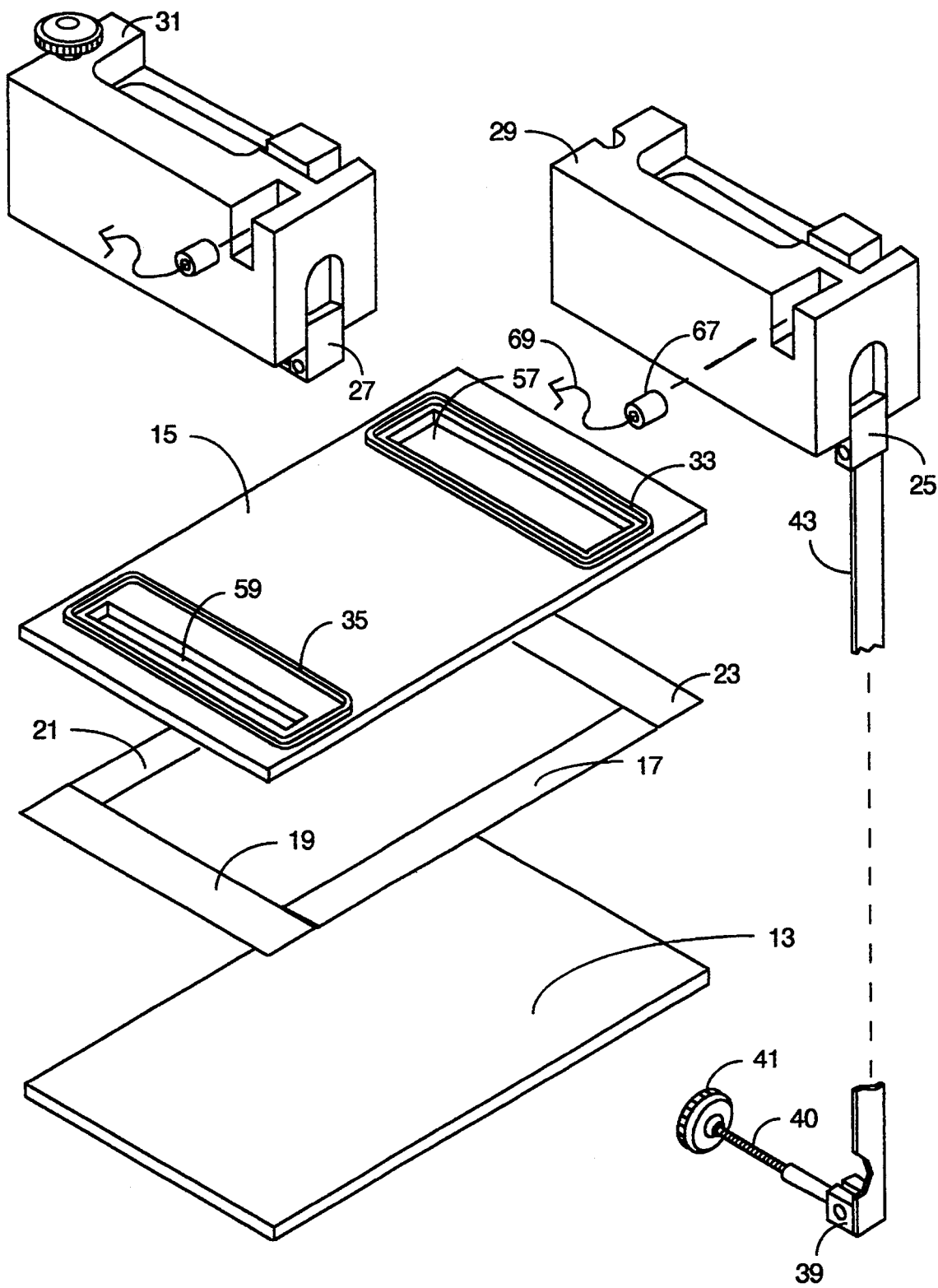
FIG. 2 is an exploded isometric assembly of the embodiment of FIG. 1.
Figure 4:
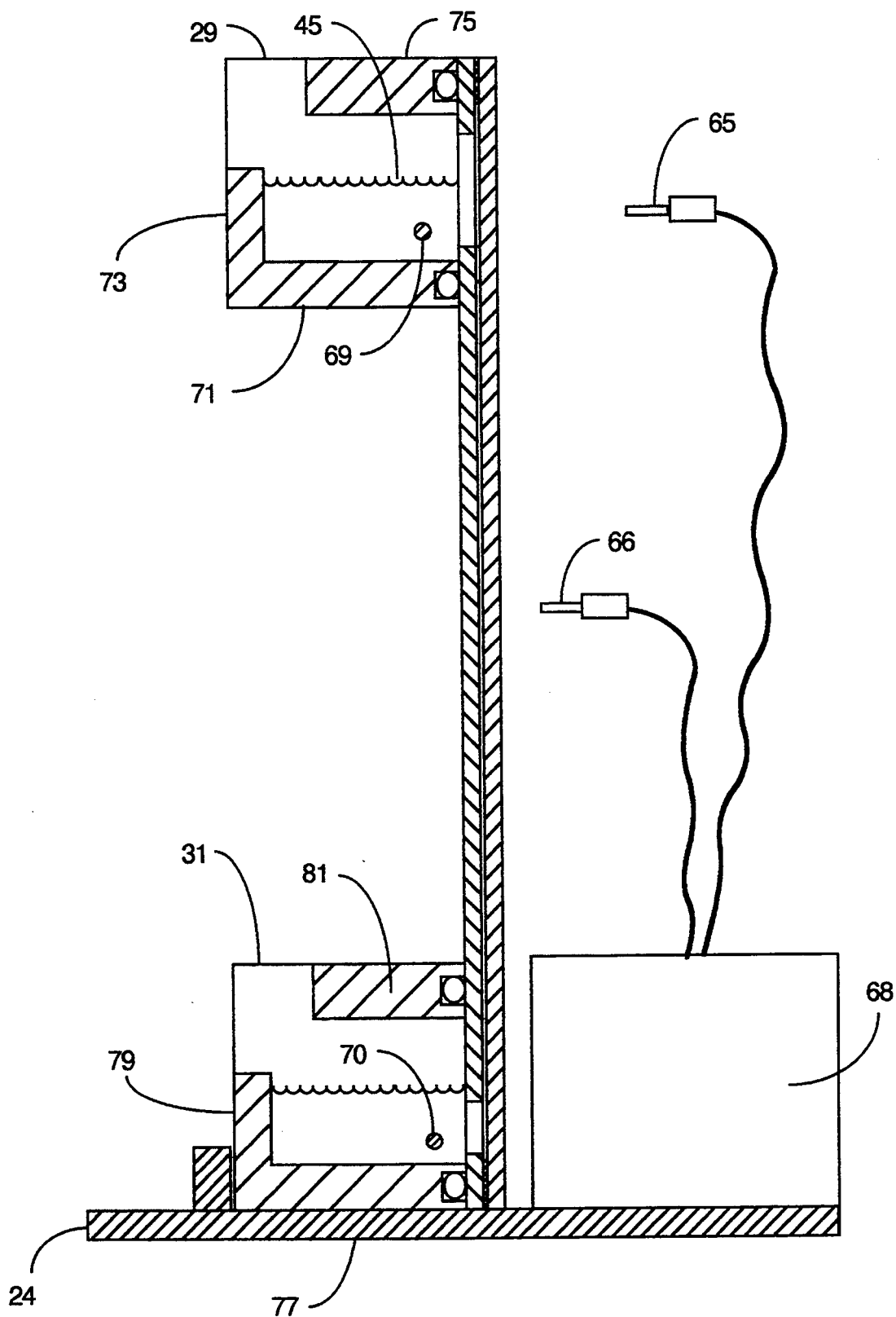
FIG. 4 is the section shown in FIG. 3A rotated to vertical orientation.
Figure 5A:
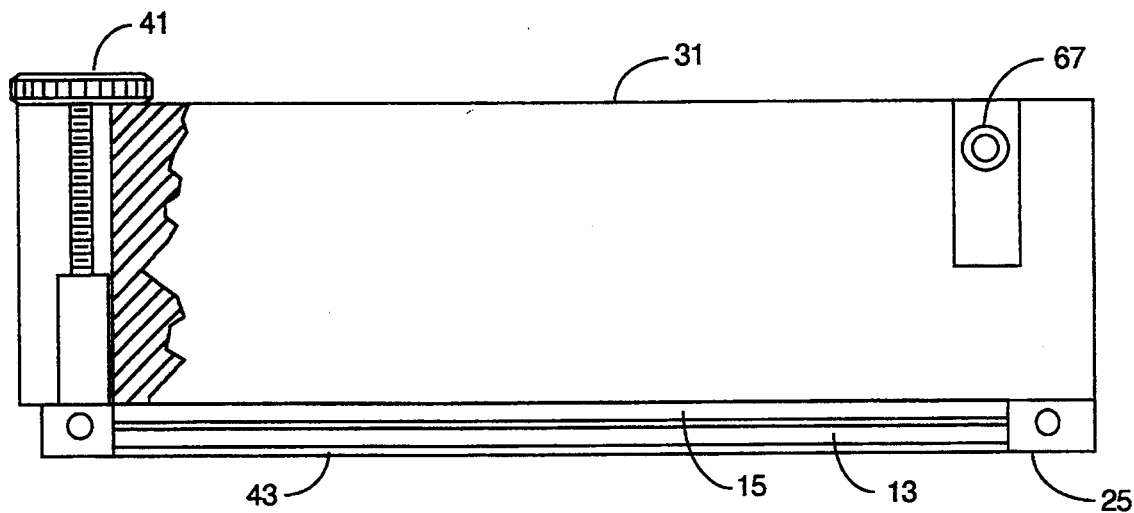
FIG. 5A is an end view of the assembly shown in FIG. 1 from the vantage of arrow 12.

As is described further below, the ability to operate either vertically or horizontally allows polyacrylamide gels to be cast horizontally and operated vertically as well as horizontally, which solves the problem of right-angle sample wells, FIG. 2 is an exploded view of the assembly of FIG. 1. FIG. 3A is a section view taken along line 3A—3A of FIG. 1. FIG. 4 is the same section shown in FIG. 3A moved to a vertical orientation and resting on a stand. FIG. 5A is an end view of the apparatus in the direction of arrow 12 of FIG. 1.

The detailed construction of the electrophoresis apparatus in the preferred embodiment is best illustrated by the exploded view of FIG. 2. A lower glass plate 13 forms a base for the apparatus. An upper glass plate 15 is spaced apart from plate 13 by edge spacer seal strips 17, 19, 21, and 23, forming a space between the plates that is the thickness of the edge spacer seal strips. This is the space for casting the gel film.

Glass plates that are used in the apparatus must be uniform and free of irregularities. The length and width of the plates may be adjusted for alternative embodiments to conform to requirements for process or scanning equipment to be used. In some embodiments plates may be ground and polished, and in others float glass may be used. The thickness of the edge spacer seal strips, which establishes the thickness of a gel film to be cast is, in a preferred embodiment, about 0.5 mm. Flatness of the plates is preferably plus or minus 0.05 mm.

The preferred material for the spacer strips is PVC, although polystyrene and some other materials are useful as well. Alternative to separate strips, a window gasket can be cut to fit as one large piece. A window gasket has the added advantage of preventing leakage that could conceivably occur when four individual strips are used but do not entirely meet. The spacer strips are positioned between the glass plates and go completely around the circumference, as seen in FIG. 2.

Buffer access to the gel film in the apparatus is by two elongated openings 57 and 59 in glass plate 15, both of which penetrate to the space between plates 13 and 15 within the area bounded by strips 17, 19, 21, and 23. Buffer reservoirs 29 and 31, which are, in the preferred embodiment, injection molded plastic, seal to upper plate 15 over openings 57 and 59 respectively to form reservoirs for buffer to wet the ends of the gel film cast between the plates.

In the preferred embodiment a liquid-tight seal is formed between the buffer reservoirs and upper plate 15 in assembly by means of O-rings 33 and 35. In other embodiments flat seals may be used, or polymeric adhesive sealing materials may also be used.

Figure 5B:
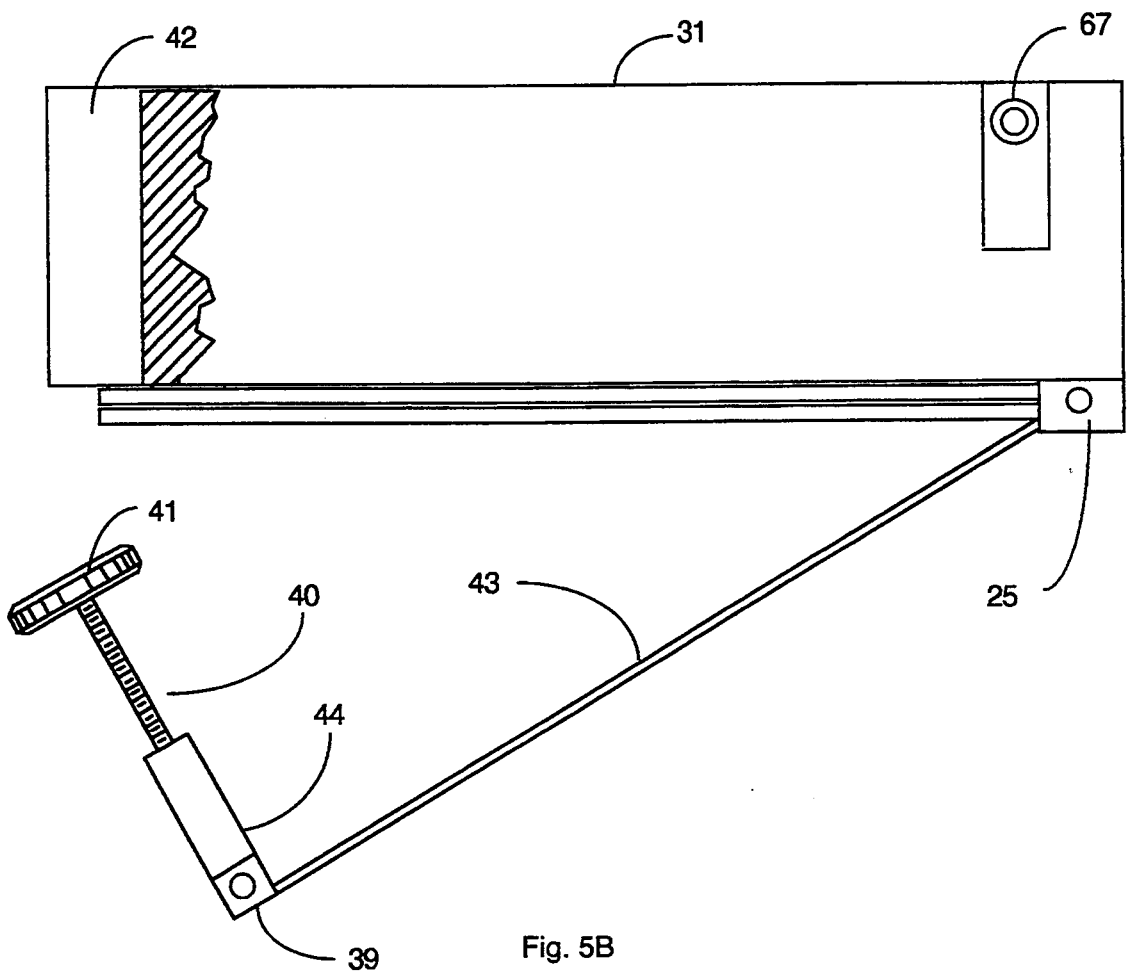
FIG. 5B is the end view of FIG. 5A with the clamping assembly opened.

Each of buffer reservoirs 29 and 31 has a clamp arrangement for holding the glass plates in assembly and sealing the reservoirs to the upper glass plate. FIG. 5A shows the clamping apparatus of reservoir 31 in a closed position. FIG. 5B shows the clamping apparatus unfolded. The clamping apparatus comprises a hinge 25 that is attached to the lower front of buffer reservoir 31. This hinge attaches at its other side to a strap 43, which terminates in a second hinge 39. The double hinges allow the clamp assembly to fold easily around the glass plates. An extension element 44 extends from hinge 39 and ends in a threaded rod 40 which is capped by a threaded knob 41. When the clamping assembly is in locked position, strap 43 rests under glass plates 13 and 15. The length of threaded shaft 40 fits into a slot 42 that extends the height of buffer reservoir 29, as seen in FIG. 5A and FIG. 5B. Tightening the threaded knob exerts force upon the buffer assembly that is transmitted to seals, spacer strips and the glass plates, locking them firmly together. With glass plates 13 and 15 held tightly together and against the spacer strips, a precise space is created for the polyacrylamide gel.

Referring to FIG. 3A, the following description uses buffer reservoir 29 as an example. Groove 32 in the bottom of the buffer reservoir, containing O-ring 33, goes completely around the circumference and encloses opening 57 in glass plate 15. O-ring 33 provides a liquid-tight seal by virtue of reservoir 29 being compressed against glass plate 15. Materials poured into the reservoir thus have egress only into the space between glass plates 13 and 15, bounded at their furthest edge by spacers 17, 19, 21, and 23 at the outside edges of glass plates 13 and 15, and by O-rings 33 and 35.

In the preferred embodiment, a platinum wire electrode is provided within the volume of each buffer reservoir to provide electrical termination for the voltage needed to accomplish electrophoresis. Electrode 69 in reservoir 29 is positioned to be below fluid level 45 and to extend substantially across the length of the reservoir. Each electrode leads to a connector plug, such as plug 67 in FIG. 2, which is staked through a wall section 72 of buffer reservoir 29, within a protective groove 74, and provides connection to an external cable for connecting to a power supply in operation. A similar plug is mounted in reservoir 31 for connection of electrode 70.

FIGS. 3A and 4 demonstrate unique construction of the wall sections of buffer reservoirs 29 and 31, which allows the apparatus to be operated in either vertical or horizontal orientation. When the apparatus is horizontal, as it is in FIG. 3A, wall portion 71 in buffer reservoir 29 acts as a side wall, wall portion 73 is a top wall, and these two wall portions are contiguous. Wall section 75 of buffer reservoir 29 is a Bide wall, and fluid level 45 is maintained slightly below the top of wall section 75. When the apparatus is turned to a vertical orientation, as Been in FIG. 4, side wall 71 becomes the bottom of the fluid-containing reservoir, wall section 73 becomes the side and wall section 75 becomes the top. Here the fluid level is slightly below the top (in a vertical orientation) of wall section 73. The walls are constructed such that with a 90-degree turn in orientation, the apparatus provides all the requirements for an electrophoresis operation, these being that the ends of the gel are wet by buffer, and the electrodes are submerged.

The opening between wall 73 and wall 75 of buffer reservoir 29 provides an access port in the buffer reservoir at an upper corner of the reservoir, providing access to the interior in assembly for operations such as pouring liquid gel and adding buffer solution. Walls 77, 79, and 81 are similarly arranged for buffer reservoir 31, and the opening between wall 79 and wall 81 provides an access port to the interior of buffer reservoir 31, in the same upper corner. These access ports remain above the level of buffer solution in the reservoirs both when the apparatus is horizontal and when it is vertical, provided the apparatus is arranged vertically such that the access openings of both buffer reservoirs remain in an upper corner. Of course there are several ways the ports might be arranged to accomplish this purpose, as long as there is an upper wall element for each reservoir with the apparatus in the horizontal position that becomes a side wall element with the apparatus in the vertical position.

Referring to FIG. 3A, openings 57 and 59 in the preferred embodiment are not the same dimension in the direction of the length of the apparatus. It is necessary that edge 58 of opening 59 be to the left of edge 83 of wall portion 79 of buffer reservoir 31, assuming the left reservoir will be the lower reservoir of FIG. 4. If this is not when the apparatus is placed in the vertical orientation, the lower end of the gel film will not be wetted, because edge 58 of opening 59 defines the lower end of the gel film.

Figure 6:
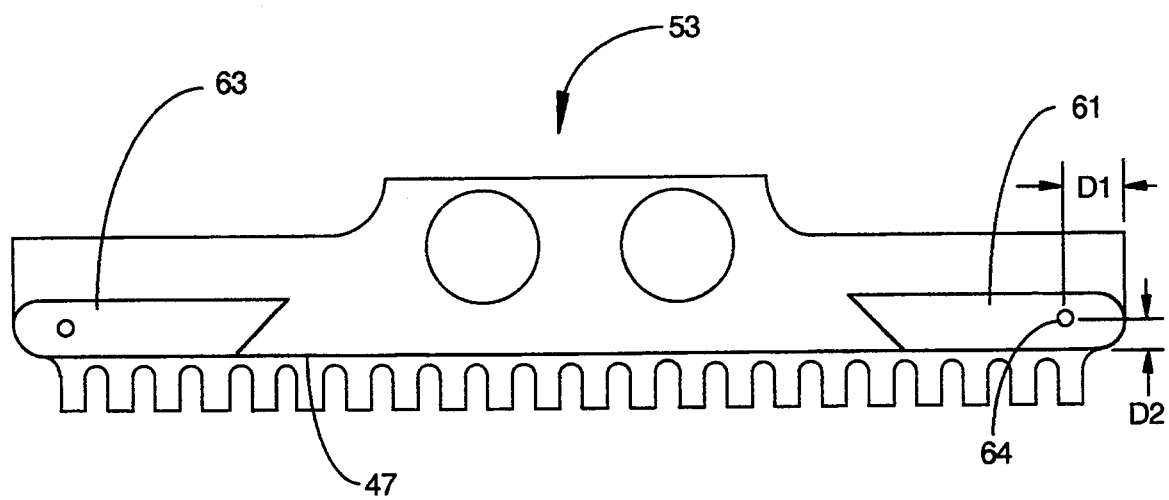
FIG. 6 is a plan view of a comb for forming sample wells.

After acrylamide monomer is poured, a unique comb 53, shown in plan view in FIG. 6, is inserted into buffer reservoir 29 and between glass plates 13 and 15, as shown in FIGS. 3A and 3B. The comb has a row of teeth that, when positioned in the acrylamide monomer, with the gel allowed to form around them, leave sample wells for injection of sample material. A preferred material for comb 53 is Delrin, which has a property of not harboring oxygen. Materials that harbor oxygen on the surface prevent formation of the gel at the interface between the comb and the monomer.

Comb 53 is shown in enlarged detail in FIG. 6. The comb teeth have a draft of about two degrees (not shown) that facilitates removal from the gel, and also has two cam levers 61 and 63 that assist in removal of the comb from the polymerized gel. In closed position, as shown in FIG. 6, the forward edges of the cam levers are colinear with an edge 47 of the body of the comb, which provides a shoulder for positioning the comb in opening 57 against edge 85. After the gel forms, the comb is dislodged for removal by operating these levers. The cams push against edge 85 of opening 57 in glass plate 15, shown in FIG. 3B, and move the comb a distance equal to the difference in distance from pivot point 64 to the edge of the comb, and from pivot point 64 to the edge of the rounded end of the cam lever. that is, D1–D2. This is just enough to dislodge the comb sufficiently for removal. This slow and uniform initial withdrawal of the comb allows the sample wells to remain intact.

Polymerization of the poured monomer should preferably occur directly against the comb surface in order for sharply defined sample wells to form and in order for those sample wells to maintain their integrity when the comb is removed, which is an intricate step much affected by several different factors. After the gel has formed, the comb is carefully removed and the sample wells left by removal of the comb, corresponding to the locations of the teeth, are ready to receive sample material. This is a crucial stage in the procedure, as the very small portions that are left in the gel between the sample wells are easily broken off.

STEPS IN USING THE APPARATUS

Typically, several preparatory steps are performed before assembling the electrophoresis apparatus. The glass plates are prepared by cleaning and thoroughly drying and inspecting for chips or cracks. O-rings 33 and 35 are mounted into the grooves at the bottom of buffer reservoirs 29 and 31 respectively. Spacer strips 17, 19, 21, and 23 are placed at the edges of glass plate 13 and positioned so as to lie flat against the glass and flush with other strips. Glass plate 15 is then placed on top of glass plate 13. The buffer reservoirs are located on top of openings 57 and 59 in glass plate 15, being sure again that all outside edges are flush. The apparatus is then clamped together by the clamping assemblies and locked by tightening the threaded knobs. The clamping assemblies serve to align the plates to one another, as well as to urge them together.

Before assembly the glass plates are treated with a methanol solution of a wetting agent, such as Brij 58. This treatment allows the monomer solution to wet all the surfaces in the space between the plates to avoid formation of bubbles or pockets.

The assembly at this point is still in a horizontal orientation and has been assembled and locked. In the apparatus of the preferred embodiment acrylamide monomer is poured with the apparatus horizontal. Casting the monomer in a horizontal mode avoids problems that are known to occur when monomer solution is poured in a vertical mode, such as leakage due to depth pressure head, After pouring the monomer, comb 53 is inserted in opening 57 of buffer reservoir 29, as shown in FIG. 3B. The comb is positioned such that edge 47 and cam levers 61 and 63 are against edge 85 of opening 57 in glass plate 15, The comb teeth are positioned between the glass plates. Once the gel has polymerized, comb 53 is carefully removed. By operating levers 61 and 63, the rounded ends of the levers push the comb gradually away from edge 85, and withdraw the comb gently from the sample wells formed.

At this point the apparatus is typically placed on a stand 24, as shown in FIG. 4, in a vertical orientation for the pouring of buffer solution, although buffer solution can be poured as well in the horizontal orientation. FIG. 4 shows the apparatus vertical and holding buffer solution at a depth just below the top of side walls 73 and 79 in buffer reservoirs 29 and 31 respectively. The depth of the buffer solution is not critical, as long as the buffer reservoirs hold buffer solution at a level to wet the ends of the gel with the apparatus oriented vertically, as shown in FIG. 4, or horizontally, as shown in FIG. 3, and electrodes 69 and 70 are fully immersed in either orientation. As previously described, in the vertical orientation as well as in horizontal orientation, the requirements for electrophoresis are met; that is, the ends of the gel film are wetted, and the electrodes are submerged.

Through the buffer solution, usually by injection, the wells formed by the comb are loaded with sample material. Loading the samples with the buffer solution already in place has been found in practice to provide for more precise placement. Also, pouring buffer after samples are loaded tends to displace the samples.

After the sample wells have been loaded, a power supply 68 is connected. Again referring to FIG. 4 and FIG. 2, connector 65 is inserted into plug 67 to power electrode 69 in buffer reservoir 29, and connector 66 is similarly connected to electrode 70 in buffer reservoir 31. The circuit thus created supplies 54V from six 9V batteries in power supply 68. The voltage is kept low in the interest of operator safety. The low voltage thus applied has been found in trials to be adequate to accomplish movement of sample material into the polyacrylamide gel.

After the sample material has been moved into the gel by application of the low voltage, the apparatus is turned once again to a horizontal orientation and placed in the scanning instrument. The assembly of FIG. 1 shows a heat sink and laser dump element 49 that is placed on top of glass plate 15 after the apparatus is placed in the scanning instrument. The laser dump provides an opaque panel that prevents the laser beam from escaping the top of the apparatus. In addition to shielding the laser beam, the heat sink and laser dump assembly also absorbs heat generated by electrical current through the gel in electrophoresis operations, and provides for a uniform temperature across the apparatus. Heat sink and laser dump 49 also has registers (not shown) for correctly positioning the electrophoresis apparatus in the scanner.

Within the scanning instrument, high voltage is applied via cables from a high voltage power supply that is an element of the scanner, with the cables plugged into the same plugs used for connecting low voltage power supply 68 in the vertical orientation. The high voltage, on the order of 1000 volts and higher, promotes electrophoresis, causing the sample material in each well to traverse the gel and separate into distinct bands, readable by a laser within the scanning instrument.

After the electrophoresis operation, the apparatus is removed from the scanning instrument and heat sink and laser dump assembly 49 are set aside. The apparatus is disassembled and cleaned and made ready for use again.

Figure 7:
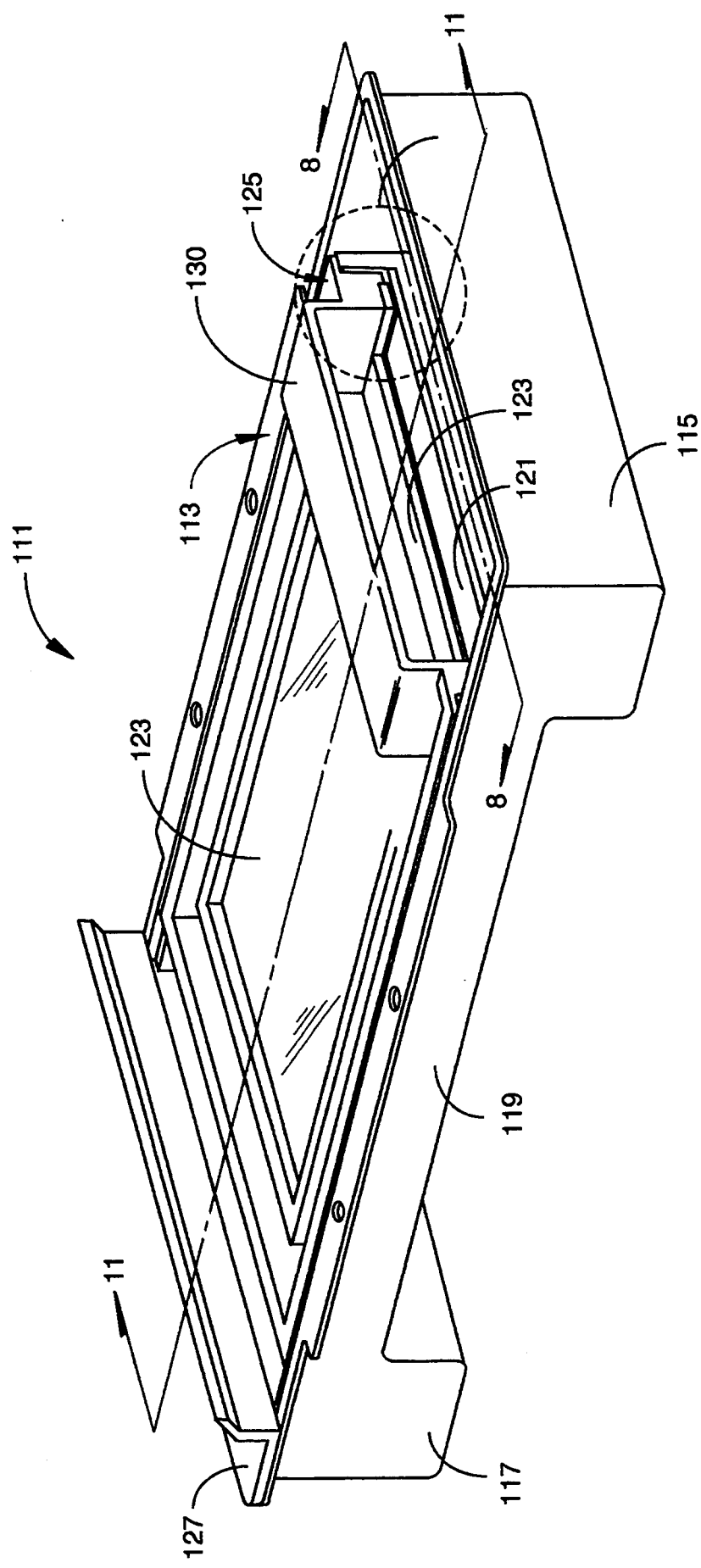
FIG. 7 is an isometric view of an alternative embodiment of the present invention.

FIG. 7 is an isometric view of an assembled polyacrylamide gel apparatus 111 according to the present invention. The apparatus has a molded tray 113 having electrode wells 115 and 117 at the ends and a center section 119 above the lower level of the electrode wells. The tray in a preferred embodiment is injection molded of opaque ABS material, although several other materials would be usable, such a polycarbonate, acrylic, and some vinyl compositions. A first glass plate 121, not seen in FIG. 7, is sealed into an opening in the tray.

A second glass plate 123 is sealed into an opening in a molded upper structure 125. The upper structure is molded from KODAR ™ PETG material to be transparent. The assembly of the upper structure and the upper plate is placed on spacer strips over the first glass plate which is sealed to tray 113. The spacer strips space the second glass plate apart from the first glass plate by an amount to be the thickness of a polyacrylamide gel that is subsequently cast between the plates. A typical thickness is about 0.5 mm.

The assembly of the upper structure to the lower structure includes flexible seal strips along the sides, and the assembly is held in contact by clamps (not shown) while a gel is cast and the unit is subsequently used for electrophoresis. After use, the clamps are removed, the upper and lower structures are separated at the gel film, the parts are cleaned, and the parts are then ready to be reused. The upper and lower structures with their sealed-in glass plates become integral structures that are not again separated.

Figure 8:
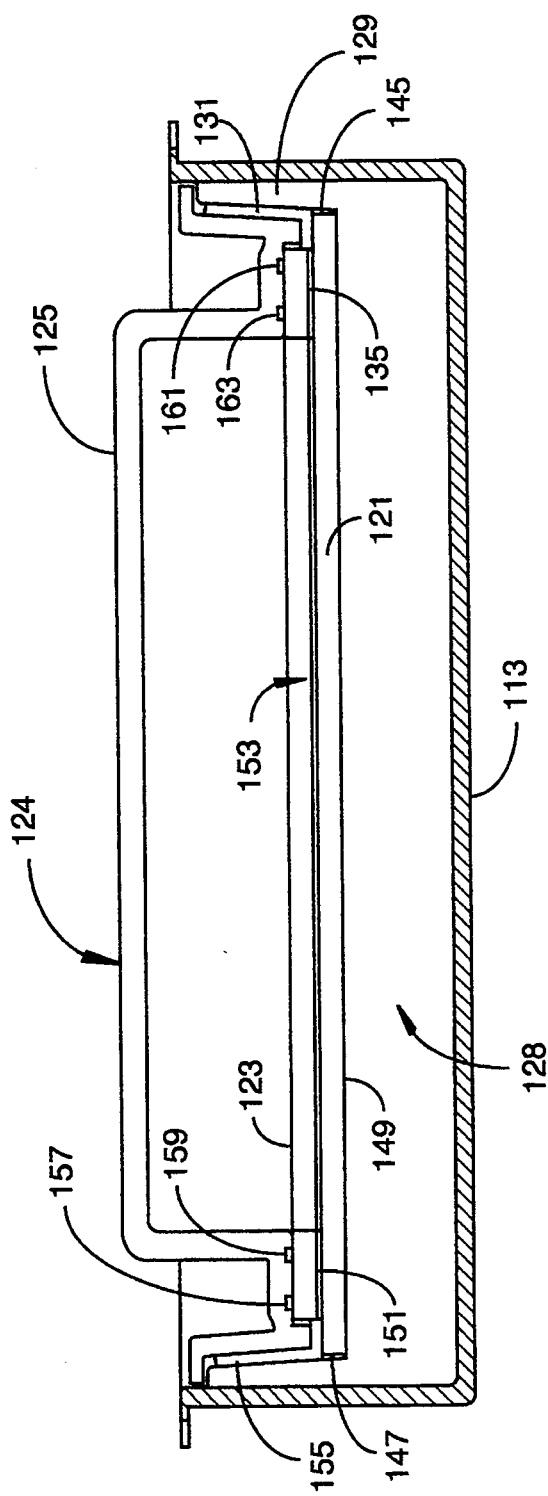
FIG. 8 is a section view of the apparatus of FIG. 7 taken along line 8—8 of FIG. 7.

FIG. 8 is an elevation section view taken along section line 8—8 in FIG. 7. Upper structure 125 and glass plate 123 are separately sealed together to form an upper rigid assembly 124 using Loctite 350 ™ UV curable sealant. To accomplish this subassembly, molded structure 125 is placed upside down, sealant is flowed into molded channels such as channels 157, 159, 161 and 163, and into channels across the width not seen in FIG. 8, plate 123 is placed in position, and the unit is placed into a UV oven to irradiate and cure the sealant.

In a manner similar to the assembly of structure 125 and plate 123, tray 113 and plate 121 are sealed together to form a rigid assembly 128. Sealant is flowed along the edges of plate 121 at positions 145 and 147, and also in channels (not shown in FIG. 8) across the width of tray 113 where plate 121 contacts the tray. These parts are then placed in a UV oven and illuminated to cure the sealant. When the two rigid assemblies are brought together, flexible seal strips 131 and 155 are placed along the edges, and spacer strips 135 and 151 are placed along the length of the sides to space apart the glass plates. The seal strips in this embodiment are made of closed-cell silicone foam material, which is chemically inert to the reagents and other materials used in electrophoresis. The assemblies are held together for use by clamps (not shown) as described above.

Figure 9:
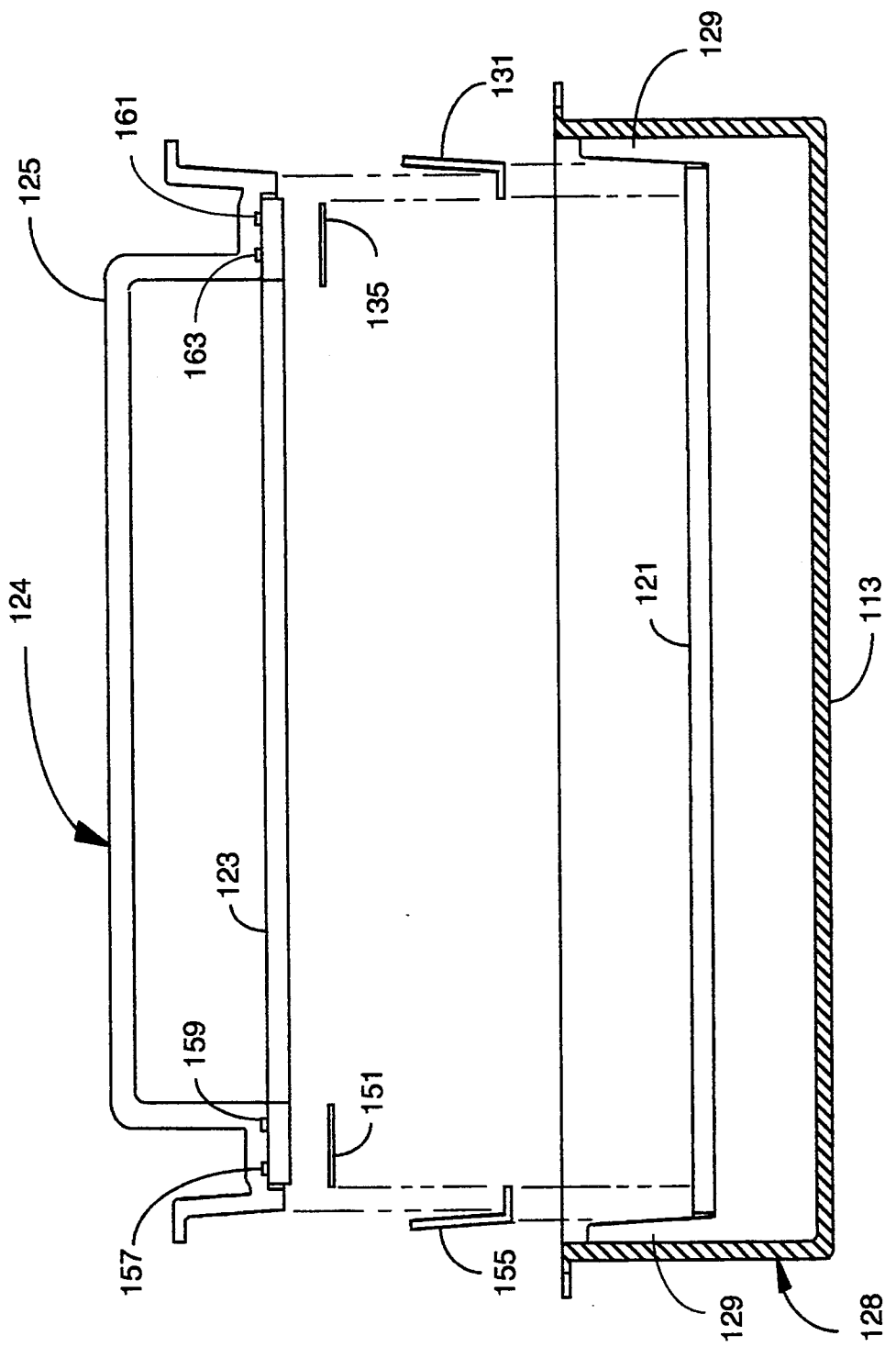
FIG. 9 is an exploded view of the elements shown in FIG. 8.

FIG. 9 is the same section as FIG. 8, but the rigid assemblies, seal strips, and spacer strips are shown in exploded view to better illustrate the arrangement of elements. As is more clearly seen in FIG. 9, lower rigid assembly 28, including tray 113 and glass plate 121 has a molded cradle configuration 129 for receiving upper rigid assembly 124, which includes molded upper structure 125 and glass plate 123. Spacer strips 135 and 151, and seal strips 131 and 155 are placed in position on lower structure 128 before the upper structure is urged into position compressing the seal strips.

Upper molded structure 125 also has a hood portion 130 (FIG. 7) to add to the configuration of well 115 so well 115 may hold buffer solution at a level to wet the ends of a gel cast between the plates with the apparatus horizontal as shown, or with the apparatus oriented vertically as described further below. A second hood element 127 is sealed to tray 113 at the end with well 117 in a manner to add to the configuration of well 117, so well 117 may also hold buffer solution at a level to wet a gel cast between the glass plates with the tray in either vertical or horizontal orientation.

Figure 10:
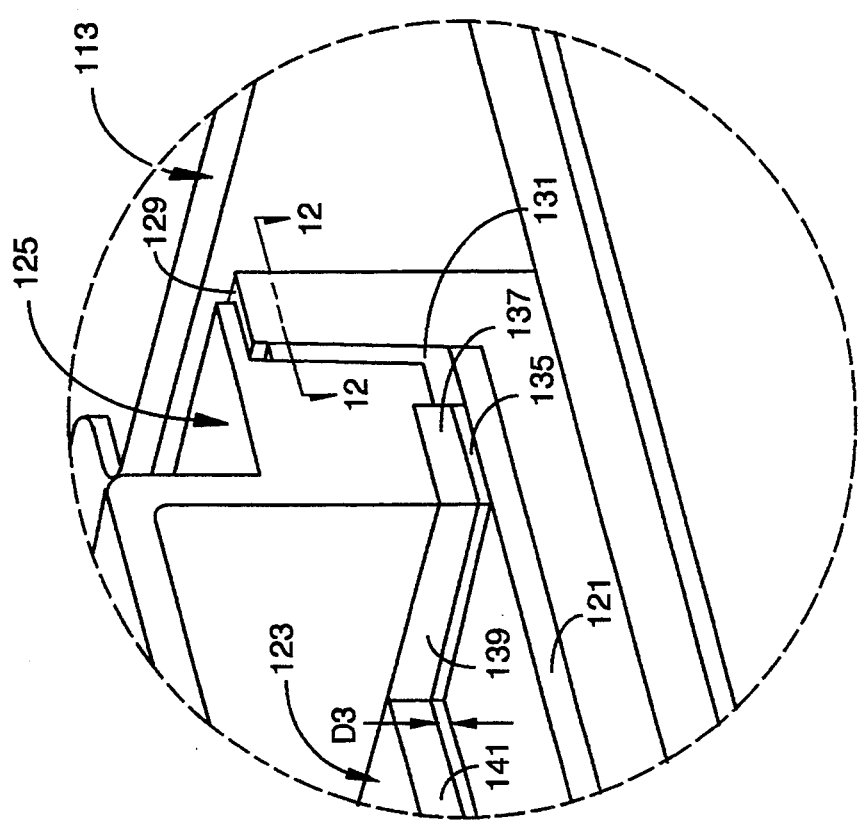
FIG. 10 is a magnified view of the area of FIG. 7 within dotted circle 10.

FIG. 10 is an enlargement of the area shown by dotted circle 10 in FIG. 7 to better illustrate the arrangement of elements at the interface between the upper and lower sections of the assembly. Flexible strip 135 is shown sandwiched between sloped sides of upper molded structure 125 and molded tray 113. Spacer strip 135 is shown between glass plates 121 and 123, providing spacing D3 between the plates for casting a polyacrylamide gel. This dimension is typically about 0.5 mm.

Another important feature that may be seen in FIG. 10 is that upper glass plate 123 has a rectangular notch. From end 137 the plate is cut away along surface 139 back to surface 141, and is similarly cut away on the opposite side of the tray (not shown). The purpose of the rectangular notch is to facilitate wetting of the end of a gel film cast between plates 121 and 123, in space 143, with the apparatus in either a horizontal or a vertical orientation. This feature is described in further detail below.

Figure 12:
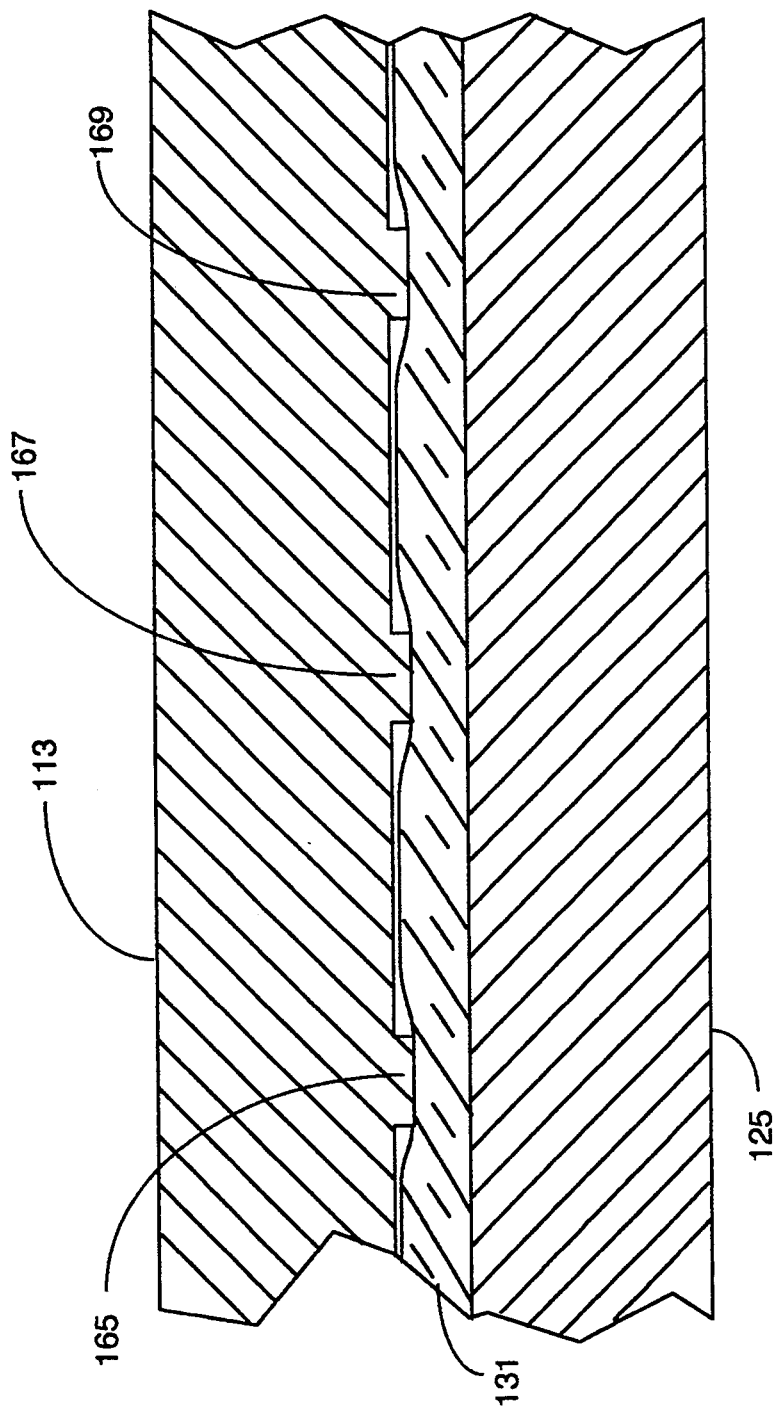
FIG. 12 is a magnified partial section view taken along line 12—12 of FIG. 10.

In the preferred embodiment there are compression ribs molded into the cradle structure of the tray, along the surfaces contacting the seal strips, for compressing the seal strip material in distinct short bands, rather than along the full length of the seal strips. This feature is illustrated in FIG. 12, which is a partial plan section view taken according to section line 12—12 of FIG. 10, greatly magnified. Flexible seal strip 131 is shown compressed between wall portions of tray 113 and molded structure 125, and compressed by compression ribs 165, 167, and 169. It has been found in practice that compression of the closed-cell seal material along the full length requires excessive force tending to distort the assembly, and the use of ribs allows sufficient compression to form the desired leak-tight seal to isolate the buffer wells with less force. With a softer seal material in alternative embodiments, the ribs are not necessary. Alternatively, the seal strips need not be continuous, but may be short strips positioned at each of the four "corners" of the glass plate structure.

Figure 11:
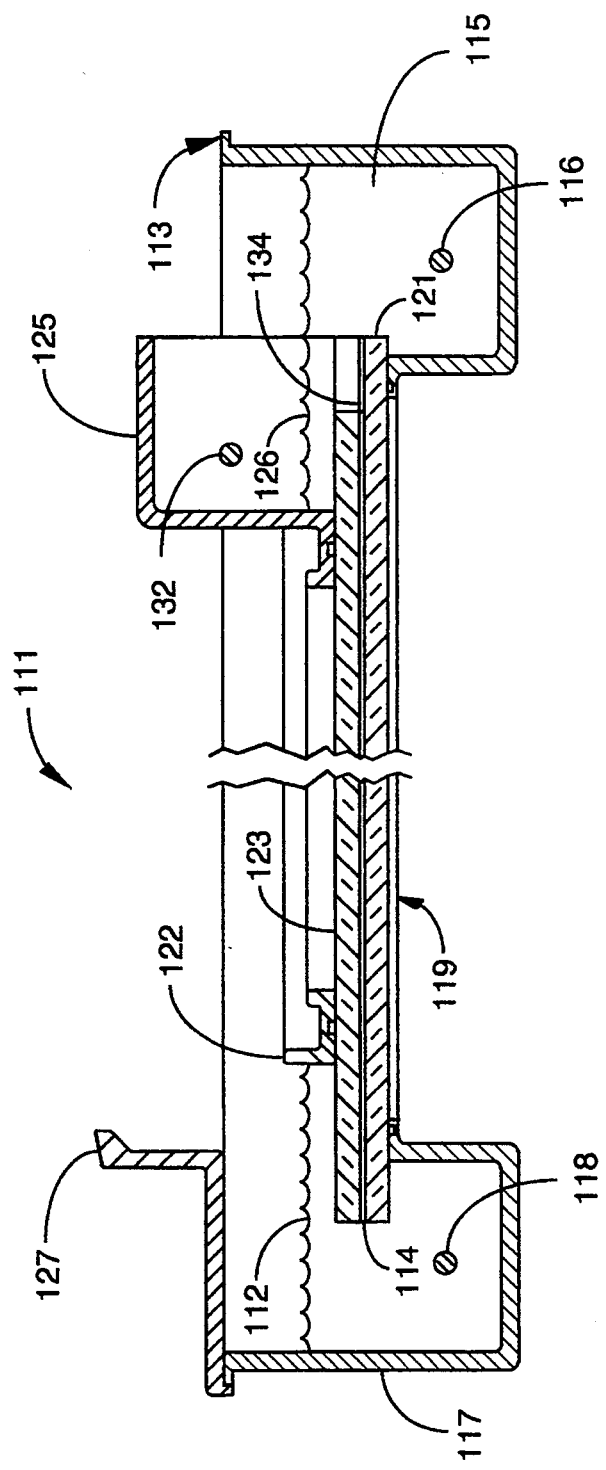
FIG. 11 is a section view taken along line 11—11 of FIG. 7.

FIG. 11 is an elevation section view taken along section line 11—11 of FIG. 7, showing details of the structure along the length of the tray in the assembled condition. The section is broken in about the center so the end elements may be shown in larger detail.

Well 117 has an electrode 118 shown within the enclosed volume of the well, and well 115 has an electrode 116. These electrodes are platinum wire in the preferred embodiment, and extend across the width of the well on each end. Provision is made (not shown) for attaching leads from a power supply to the electrodes to provide the electromotive force needed to accomplish electrophoresis. Plugs for power supply cables are not shown, but are mounted in a manner similar to that described above for the first-described preferred embodiment.

With buffer added in the horizontal orientation, the level comes up to about surface 112, and buffer is prevented from passing over the upper plate by a dam structure 122 which is part of the upper rigid assembly. The end of the gel film, shown at 114, is wetted in this condition, and electrode 118 is submerged.

Buffer in well 115 comes up to about surface 126 with the apparatus in horizontal orientation, and again the end of the film (shown at 134) is wetted, and electrode 116 is submerged.

Just as with the first-described preferred embodiment above, monomer is poured after wetting agent in the horizontal mode, and comb 53 is used to provide sample wells as the gel forms. After the gel forms and the comb is withdrawn using the cam levers described above, the apparatus may be rotated to vertical orientation.

Figure 13:
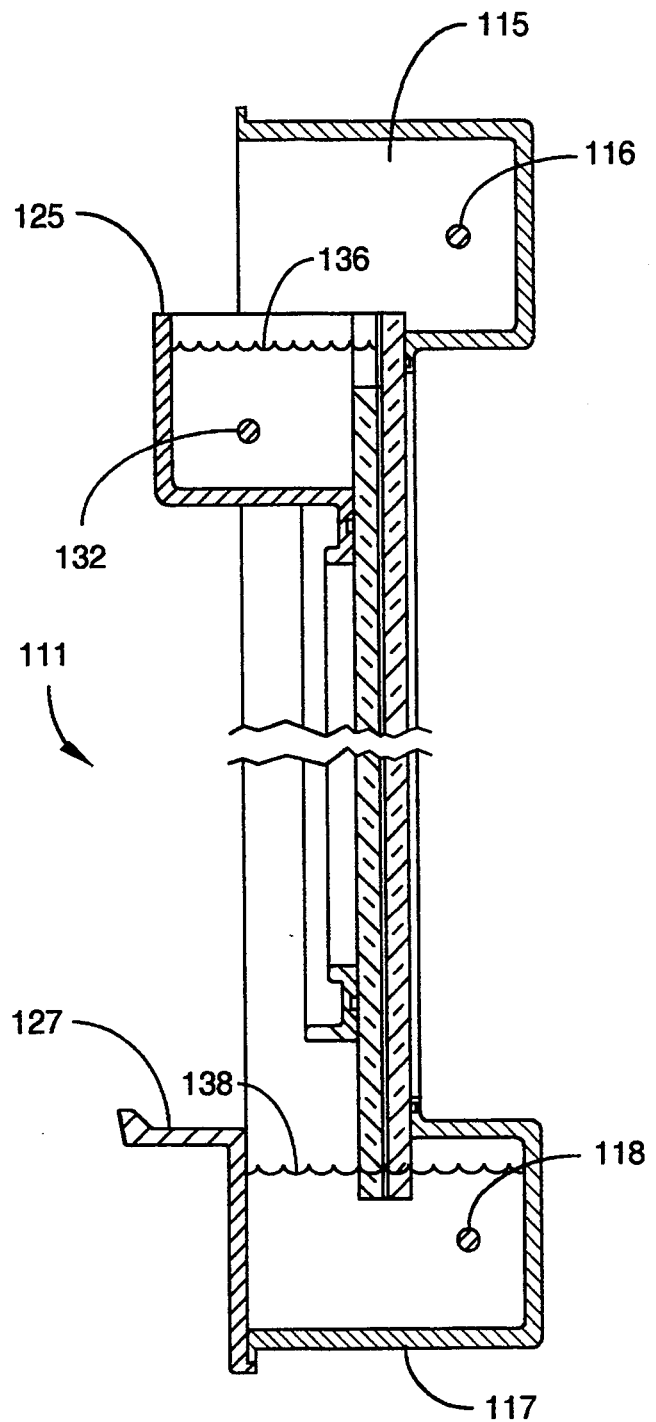
FIG. 13 is the section view of FIG. 11 shown rotated to a vertical orientation.

FIG. 13 shows the apparatus rotated to vertical for loading of sample and starting of sample material into the gel film. No stand is shown, but a stand similar to that used in the first preferred embodiment described above is used.

In the vertical orientation, hood structure 125 forms a new upper well, having a separate electrode 132, which has a separate connection than electrode 116. Buffer comes to surface 136, and electrode 132 and the end of the gel film are submerged, as required.

At the lower end, structure 127 helps to form a lower well, buffer comes to surface 138, and electrode 118 and the end of the gel film are submerged.

In the vertical orientation, sample material is loaded to the several sample wells through the buffer solution, and electrodes 132 and 118 are connected to a low voltage power supply, typically a 54V supply comprising six 9V batteries in series. As was mentioned above, it has been found in practice that 54V is sufficient to run the material into the gel, and provides a safe operating voltage for this preliminary procedure.

After running the sample into the gel, the apparatus is again rotated to horizontal, a laser dump is added, and the apparatus is placed in a horizontal scanner to perform the analytical electrophoresis. High voltage is connected to electrodes 118 and 116 to accomplish electrophoresis. After use, the apparatus may be separated at the gel film, cleaned, and re-used.

It will be apparent to one with skill in the art that there are many changes that may be made in the embodiments described without departing from the spirit and scope of the invention. There are many materials that may be substituted, for example, and apparatus may be constructed according to the invention with widely varying dimensions. The apparatus also may be used as described, but with a vertical scanner rather than the horizontal scanner described herein.

What is claimed is:

1. An electrophoresis apparatus comprising:
   a first and a second surface spaced-apart defining a volume therebetween for casting an electrophoretic gel film, said volume having a first end and a second end;
   a first electrode proximate said first end and a second electrode proximate said second end, said electrodes connectable to a power supply for establishing an electromotive force for inducing electrophoretic action;
   a first reservoir at said first end configured to hold buffer solution immersing said first end and said first electrode with said spaced-apart surfaces oriented substantially horizontally and oriented substantially vertically; and
   a second reservoir at said second end configured to hold buffer solution immersing said second end and said second electrode with said spaced-apart surfaces oriented substantially horizontally and oriented substantially vertically.

2. An electrophoresis apparatus as in claim 1 wherein said spaced-apart surfaces are surfaces of substantially flat glass plates spaced apart by seals along two edges for containing a gel-forming solution.

3. An electrophoresis apparatus as in claim 2 wherein said seals close all sides of said spaced-apart plates and said first plate has a first opening therethrough adjacent said first end and a second opening therethrough adjacent said second end, a gel film cast in the volume between the plates having an exposed end facing into each of said openings, and wherein said buffer reservoirs comprise removable enclosures sealable around said openings.

4. An electrophoresis apparatus as in claim 3 wherein each said removable enclosure comprises a structure having substantially vertical side walls and end walls for retaining buffer solution with said spaced-apart surfaces oriented substantially horizontally, a partial top wall forming a side wall when said apparatus is rotated to orient said spaced-apart surfaces substantially vertically, a sealing port sealable around one of said first and second openings through said plate, and an access port through a portion of said top wall for providing access to the volume within said enclosure.

5. An electrophoresis apparatus as in claim 4 wherein each said removable enclosure additionally comprises a one or more clamps for positioning and holding said spaced-apart plates in fixed relation and for urging said enclosure toward said first plate to accomplish a seal between said enclosure and said first plate around said opening in said first plate.

6. An electrophoresis apparatus as in claim 2 comprising a plastic molded framework for receiving and positioning said substantially flat glass plates, and said first and second reservoirs are molded into said plastic molded framework.

7. A method for separating macromolecules by electrophoresis comprising steps of:
   casting an electrophoretic gel film with a first end and a second end in a volume between a first and a second spaced-apart surface of an electrophoresis apparatus comprising a first electrode proximate said first end and a second electrode proximate said second end, said electrodes connectable to a power supply for establishing an electromotive force for inducing electrophoretic action, a first reservoir at said first end configured to hold buffer solution immersing said first end and said first electrode with said spaced-apart surfaces oriented substantially horizontally and oriented substantially vertically, and a second reservoir at said second end configured to hold buffer solution immersing said second end and said second electrode with said spaced-apart surfaces oriented substantially horizontally and oriented substantially vertically;
   forming sample wells in said electrophoretic gel film by placing a well-forming comb in the space between said first and second surfaces at one of said first and second ends while the electrophoretic gel is liquid, and withdrawing said comb after said gel is formed;
   filing the first and second reservoirs with buffer solution;
   positioning the electrophoresis apparatus vertically;
   placing a sample to be electrophoresed in one of the sample wells;
   connecting the electrode means to a power supply and running the sample into the gel;
   placing the electrophoresis apparatus horizontally; and
   separating macromolecules in the sample by electrophoresis.

8. The method of claim 7 wherein the power supply for running the sample into the gel is a first power supply operated at a low voltage not dangerous to a user, and for separating macromolecules by electrophoresis with the apparatus placed horizontally the electrodes are connected to a second power supply operated at a high voltage.

9. The method of claim 7 wherein said step of separating macromolecules in the sample by electrophoresis is performed in an automatic analytical scanner with the electrophoresis apparatus positioned horizontally.

* * * * *